United States Patent
Moon

(10) Patent No.: US 10,856,831 B2
(45) Date of Patent: Dec. 8, 2020

(54) MAMMOGRAPHY DEVICE AND METHOD OF PHOTOGRAPHING OBJECT TO BE INSPECTED USING THE SAME

(71) Applicant: GENERAL ELECTRIC COMPANY, Schenectady, NY (US)

(72) Inventor: Jin Young Moon, Seoul (KR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 215 days.

(21) Appl. No.: 14/781,279

(22) PCT Filed: Sep. 30, 2013

(86) PCT No.: PCT/KR2013/008766
§ 371 (c)(1),
(2) Date: Sep. 29, 2015

(87) PCT Pub. No.: WO2014/157794
PCT Pub. Date: Oct. 2, 2014

(65) Prior Publication Data
US 2016/0278730 A1    Sep. 29, 2016

(30) Foreign Application Priority Data

Mar. 29, 2013   (KR) ........................ 10-2013-0034368

(51) Int. Cl.
*A61B 6/00*   (2006.01)
*A61B 6/04*   (2006.01)
(Continued)

(52) U.S. Cl.
CPC .............. *A61B 6/545* (2013.01); *A61B 5/107* (2013.01); *A61B 6/03* (2013.01); *A61B 6/0457* (2013.01);
(Continued)

(58) Field of Classification Search
CPC ... A61B 6/0457; A61B 6/4435; A61B 6/4441; A61B 6/467; A61B 6/502; A61B 6/545
(Continued)

(56) References Cited

U.S. PATENT DOCUMENTS 4,658,409 A    4/1987   Summ
5,099,503 A *  3/1992   Strömmer .............. A61B 6/502
                                                              378/208
(Continued)

FOREIGN PATENT DOCUMENTS

CN       1739452 A      3/2006
CN     104127202 A    11/2014
(Continued)

OTHER PUBLICATIONS

International Search Report for PCT/KR2013/008766 dated Jan. 10, 2014.
(Continued)

*Primary Examiner* — Allen C. Ho
(74) *Attorney, Agent, or Firm* — Fletcher Yoder, P.C.

(57) ABSTRACT

Disclosed herein are mammography device for X-ray photographing a breast and a method of photographing an object to be inspected using the same. The mammography device includes: a generator irradiating an X-ray; a detector facing the generator; a pressing pad moving between the generator and the detector to press an object to be inspected; a biological index deciding unit deciding a biological index of a subject; and a controller controlling a movement distance and a velocity of the pressing pad on the basis of the biological index decided in the biological index deciding unit.

9 Claims, 4 Drawing Sheets

(51) Int. Cl.
*A61B 6/03* (2006.01)
*A61B 5/107* (2006.01)

(52) U.S. Cl.
CPC .......... *A61B 6/4405* (2013.01); *A61B 6/4435* (2013.01); *A61B 6/4441* (2013.01); *A61B 6/467* (2013.01); *A61B 6/502* (2013.01)

(58) Field of Classification Search
USPC .......................................................... 378/37
See application file for complete search history.

(56) References Cited

U.S. PATENT DOCUMENTS

| | | | | |
|---|---|---|---|---|
| 5,335,257 | A * | 8/1994 | Stunberg | A61B 6/502 378/117 |
| 5,349,625 | A | 9/1994 | Born et al. | |
| 5,526,394 | A * | 6/1996 | Siczek | A61B 6/4233 378/145 |
| 5,590,166 | A * | 12/1996 | Suni | A61B 6/0414 378/196 |
| 6,768,783 | B2 * | 7/2004 | Eriksson | A61B 6/0421 378/208 |
| 6,999,554 | B2 * | 2/2006 | Mertelmeier | A61B 6/0414 378/196 |
| 7,003,073 | B2 * | 2/2006 | Andreasson | A61B 6/502 378/177 |
| 7,400,707 | B2 * | 7/2008 | Nakayama | A61B 6/0414 378/108 |
| 7,433,445 | B2 * | 10/2008 | Okada | A61B 6/502 378/37 |
| 7,545,908 | B2 * | 6/2009 | Hemmendorff | A61B 6/502 378/205 |
| 7,573,977 | B2 * | 8/2009 | Tsujita | A61B 6/56 378/197 |
| 7,613,276 | B2 * | 11/2009 | Sendai | A61B 6/0414 378/37 |
| 7,639,779 | B2 * | 12/2009 | Kashiwagi | A61B 6/502 378/165 |
| 7,656,993 | B2 * | 2/2010 | Hoernig | A61B 6/0414 128/845 |
| 7,817,773 | B2 * | 10/2010 | Stanton | A61B 6/466 378/15 |
| 7,885,379 | B2 * | 2/2011 | Meer | A61B 6/502 378/37 |
| 7,916,832 | B2 * | 3/2011 | Hara | A61B 6/4494 378/20 |
| 8,031,834 | B2 * | 10/2011 | Ludwig | A61B 6/025 378/22 |
| 8,292,824 | B2 * | 10/2012 | Okada | A61B 10/0266 600/564 |
| 8,467,495 | B2 * | 6/2013 | Okada | A61B 6/022 378/151 |
| 8,540,637 | B2 * | 9/2013 | Tokita | A61B 5/0091 600/437 |
| 8,553,837 | B2 * | 10/2013 | Johansson | A61B 6/025 378/22 |
| 8,787,522 | B2 * | 7/2014 | Smith | A61B 6/025 378/20 |
| 8,792,617 | B2 * | 7/2014 | Baetz | A61B 6/4035 378/16 |
| 8,848,865 | B2 * | 9/2014 | Nakayama | A61B 6/0414 378/37 |
| 8,876,717 | B2 * | 11/2014 | Tokita | A61B 5/0091 600/437 |
| 9,098,935 | B2 * | 8/2015 | Endo | A61B 6/463 |
| 9,131,914 | B2 * | 9/2015 | Ramsauer | A61B 6/0414 |
| 9,239,316 | B2 * | 1/2016 | Tokita | A61B 5/0095 |
| 9,282,942 | B2 * | 3/2016 | Mertelmeier | A61B 6/502 |
| 9,517,038 | B2 * | 12/2016 | Williams | A61B 6/0414 |
| 9,532,752 | B2 * | 1/2017 | Goossen | A61B 6/0414 |
| 2005/0265518 | A1 * | 12/2005 | Aubel | A61B 6/502 378/37 |
| 2006/0245541 | A1 * | 11/2006 | Aubel | A61B 6/0414 378/37 |
| 2007/0249925 | A1 | 10/2007 | Hoheisel et al. | |
| 2008/0043904 | A1 | 2/2008 | Hoernig | |
| 2008/0089472 | A1 * | 4/2008 | Yoon | A61B 6/482 378/37 |

FOREIGN PATENT DOCUMENTS

| | | |
|---|---|---|
| JP | 60-114238 A | 6/1985 |
| JP | H06261896 A | 9/1994 |
| JP | 2003-520115 A | 7/2003 |
| JP | 2005-013344 A | 1/2005 |
| JP | 2007-236805 A | 9/2007 |
| JP | 2008-086760 A | 4/2008 |
| JP | 2009-022536 A | 2/2009 |
| JP | 2010-094397 A | 4/2010 |
| KR | 2004-0031111 A | 4/2004 |
| WO | WO 01/54463 A1 | 7/2001 |

OTHER PUBLICATIONS

Extended European Search Report for European Application No. 13880638.5 dated Feb. 26, 2016.
Machine translation and Notification of Preliminary Rejection issued in connection with corresponding JP Application No. 2016-505372 dated Sep. 12, 2017.
Machine translation and First Office Action and Search issued in connection with corresponding CN Application No. 201380076744.5 dated Oct. 10, 2017.

* cited by examiner

[Fig. 1]
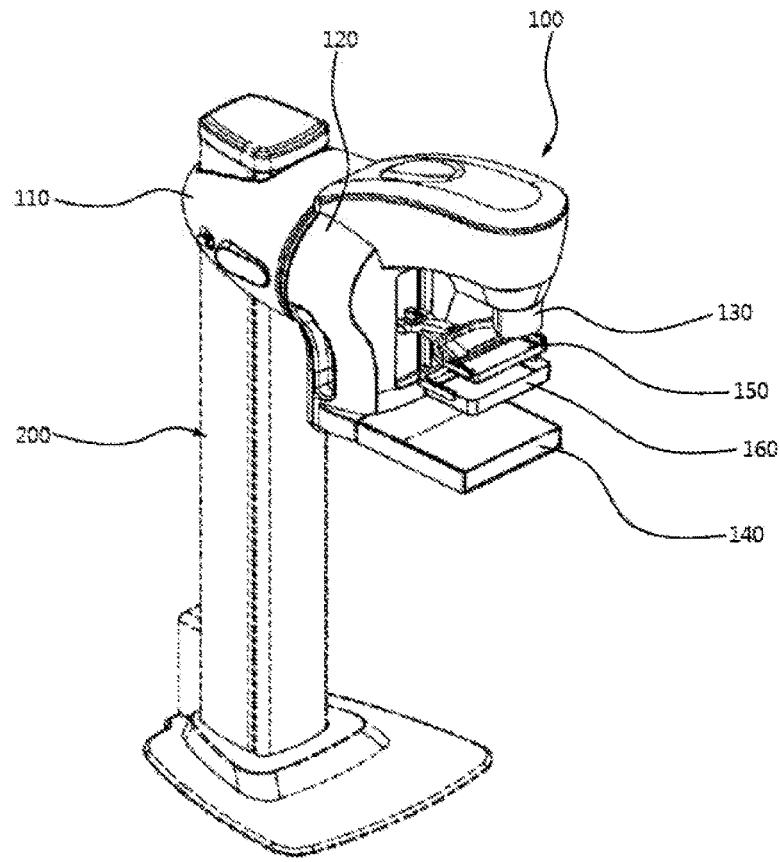
[Fig. 2]
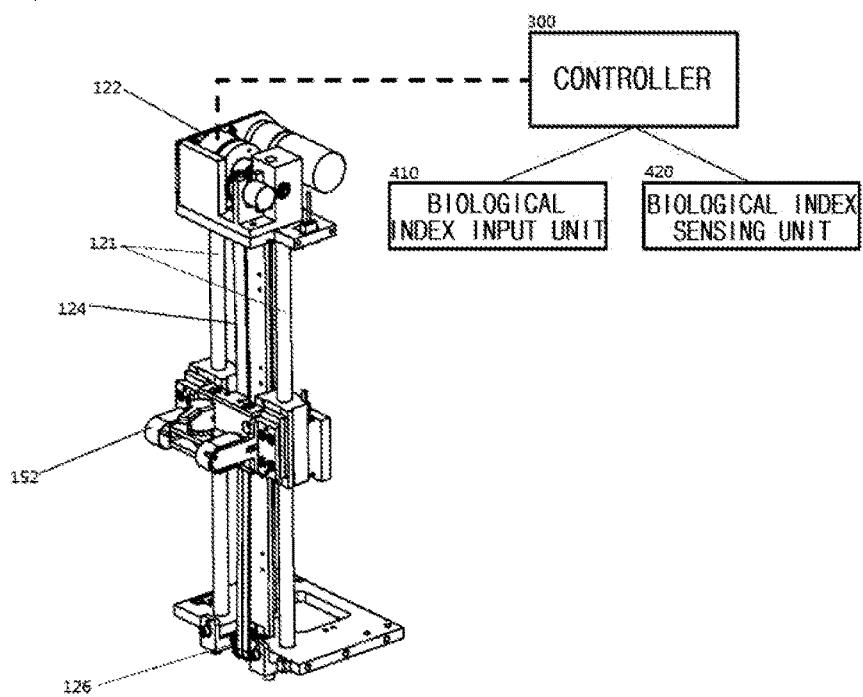

[Fig. 3]
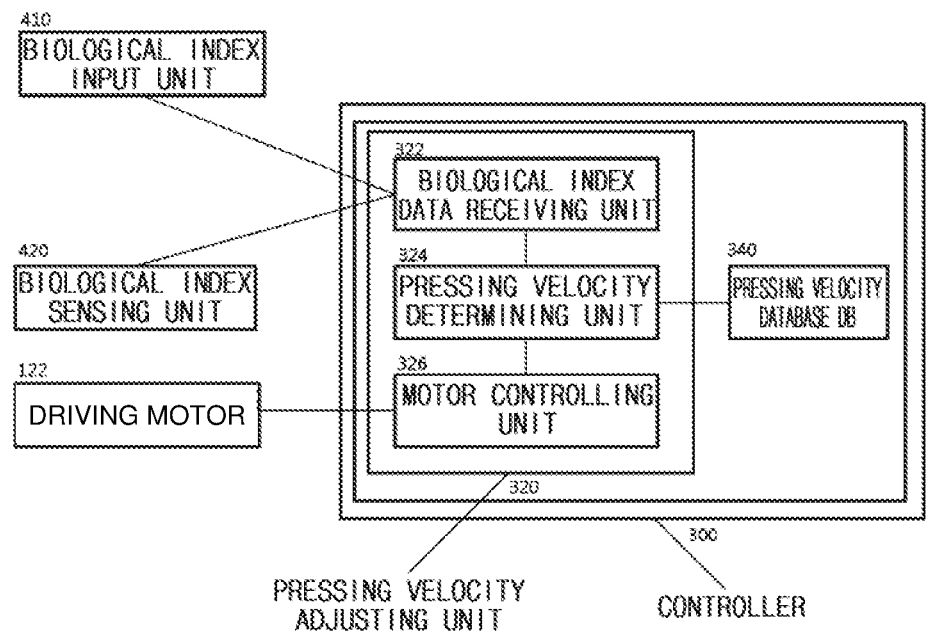
[Fig. 4]
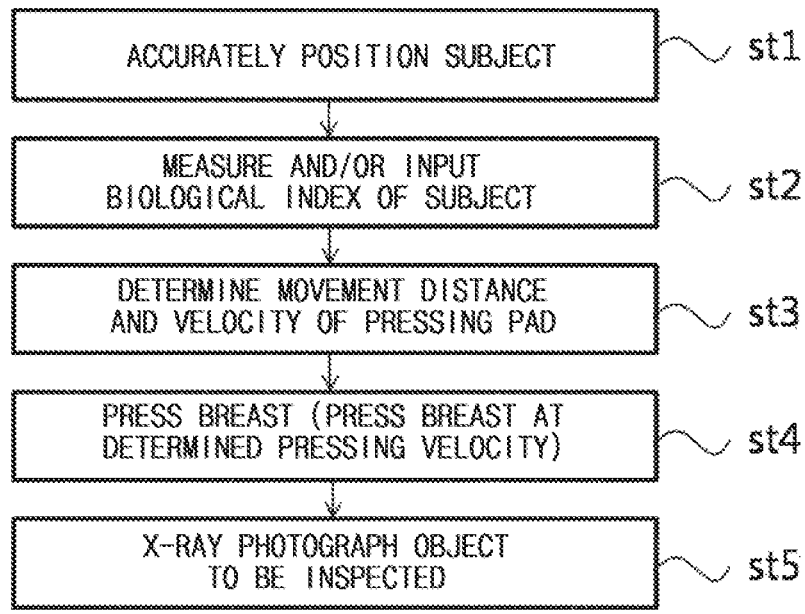

[Fig. 5]
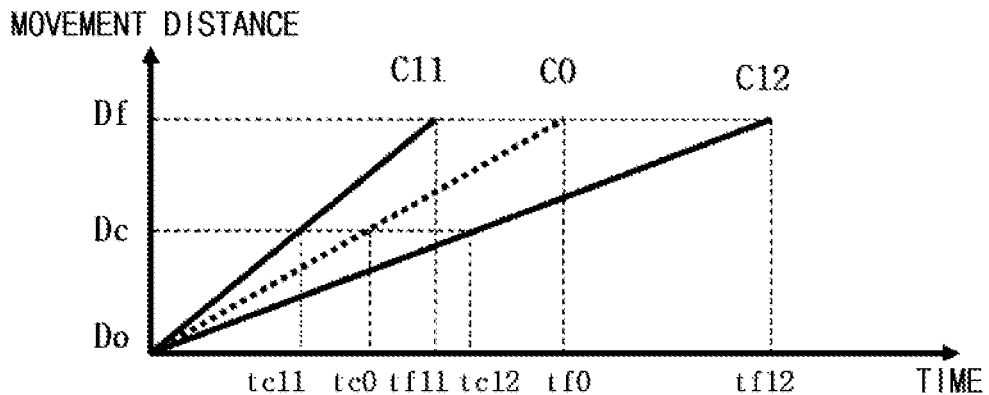
[Fig. 6]
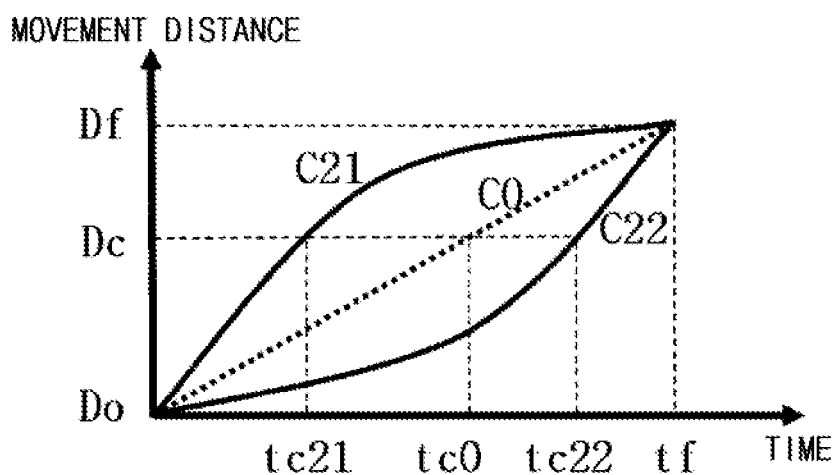
[Fig. 7]
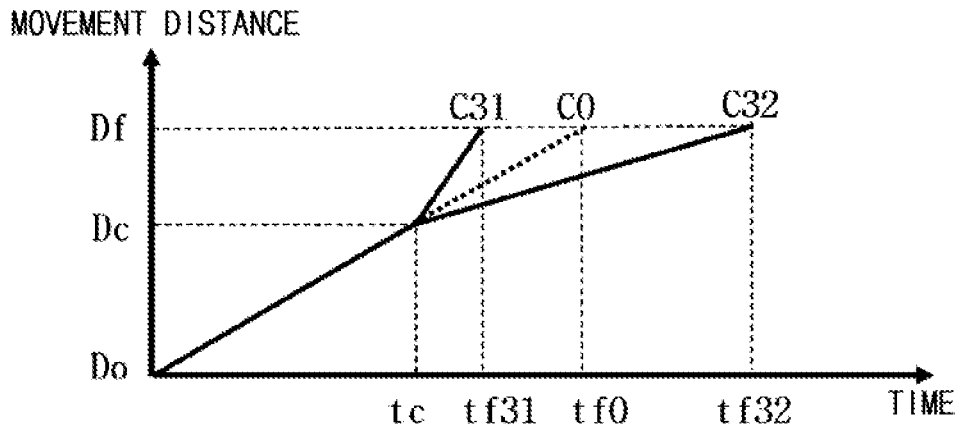

[Fig. 8]
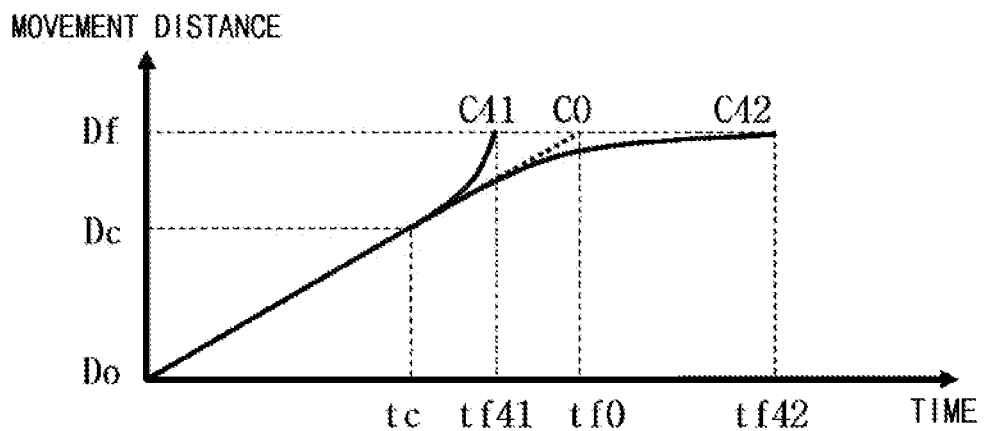
[Fig. 9]
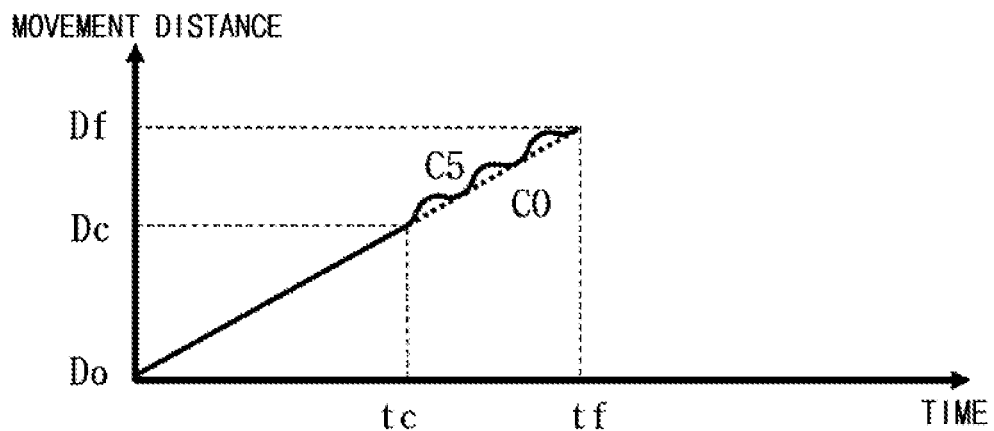

MAMMOGRAPHY DEVICE AND METHOD OF PHOTOGRAPHING OBJECT TO BE INSPECTED USING THE SAME

TECHNICAL FIELD

The present invention relates to a mammography device for X-ray photographing an object to be inspected and a method of photographing an object to be inspected using the same, and more particularly, to a mammography device capable of providing comfort to a subject by removing or minimizing pain or discomfort applied to the subject and accomplishing a high photographing accuracy, and a method of photographing an object to be inspected using the same.

The present invention is derived from research performed as a part of nano-material based multi X-ray source and tomography image system technology development of the Ministry of Knowledge Economy [Project Management Number: 10037414, Project Name Nano-material Based Multi X-ray Source and Tomography Image System Technology Development].

BACKGROUND ART

An X-ray generally indicates a short wavelength electromagnetic wave having a wavelength of 0.01 nm to 10 nm and a frequency of $30 \times 10^{15}$ Hz to $30 \times 10^{18}$ Hz. X-ray photographing is one of radiographies of projecting and displaying an inner portion of an object to be inspected by high penetration power of the X-ray. As well-known, the X-ray involves an attenuation phenomenon depending on a material, a density, and a thickness of an object, such as Compton scattering, a photoelectric effect, or the like, during a process in which it is transmitted through the object. Therefore, the X-ray photographing projects and displays the inner portion of the object to be inspected on the basis of an attenuation amount of the X-ray accumulated during a process in which the X-ray passes through the object to be inspected. To this end, a dedicated X-ray system is used.

Recently, an X-ray image technology has been rapidly evolved as a digital X-ray image technology having various advantages such as a relatively high resolution, a wide dynamic area, easy generation of an electrical signal, simple processing and storing of data, and the like, instead of a traditional analog scheme using a film while being grafted onto a semiconductor field. A digital based image technology strongly reflects a clinically environmental demand such as an early diagnosis of a disease on the basis of excellent diagnosis ability of a digital image.

Therefore, a "digital mammography", which is a breast dedicated X-ray photographing technology capable of detecting a lesion and micro-calcification for detection and an early diagnosis of a breast cancer by representing an internal structure of the breast corresponding to an object to be inspected as a high resolution image, using unique biological tissue contrast capability of the X-ray, has been introduced. The digital mammography has been rapidly spread due to unique characteristics such as image enlargement, a decrease in the number of times of photographing, an increase in a resolution, and minimization of exposure through adjustment of a luminance and a contrast ratio together with various advantages of the digital X-ray image technology.

A general mammography device mainly includes a support column having a lower end portion fixed to a bottom and having a vertical column shape and a C-arm or a device body installed on the support column so as to ascend or descend in a vertical direction and generally having a C shape or a shape similar to the C shape in which a central portion thereof is configured to be rotatable with respect to a horizontal axis. A generator irradiating an X-ray toward a lower end portion of the device body is mounted at an upper end portion of the device body, and a detector facing the generator is mounted at the lower end portion of the device body. A pressing pad that vertically and linearly reciprocates along an inner surface of the device body is installed between the generator and the detector.

In the mammography device as described above, when a subject is in a standing or sitting state at a photographing position, the device body ascends or descends and rotates with respect to the support column, such that a height and an angle of the device body are adjusted so that a breast of the subject is put at a target position on the detector. Then, the pressing pad moves toward the detector to press the breast. In this state, the generator irradiates the X-ray toward the breast and the detector, and the detector positioned behind the breast receives the X-ray passing through the breast to obtain an image.

That is, the detector generates an electric signal for each position that is in proportion to an amount of incident X-ray, and reads the electrical signal and position information and processes the read electrical signal and position information by an image processing algorithm, thereby making it possible to obtain an X-ray image of the breast for a corresponding angle. Then, the above-process is repeated while rotating the generator and the detector with the breast interposed therebetween, whereby the mammography apparatus may obtain high resolution images for the breast of the subject at various mediolateral oblique view angles.

In a general mammography device having the above-mentioned photographing principle, a critical driving mechanical for minimizing discomfort of the subject and obtaining a high quality X-ray image is a pressing operation of the pressing pad and ascending or descending and rotating operations of the device body. Particularly, since the pressing pad applies direct pressure to the breast at the time of X-ray photographing, it is directly associated with pain and discomfort felt by the subject, and since the device body determines an accurate photographing position through ascent or descent and rotation, it is directly associated with quality of the X-ray image.

Here, the pressing pad presses the breast in order to photograph the breast in a state in which the breast is pressed for the purpose of separating a lump (a lesion or a portion at which the possibility of micro-calcification is high) looking like being overlapped with a mammary gland, or the like, from the mammary gland.

However, the pressing by the pressing pad is the largest pain felt by the subject, and the pain is generally felt at different levels by the subject depending on a biological index of the subject. For example, the smaller the size of the breast, the higher the density of the breast, and the younger, the larger the pain felted by the subject.

Further, in a mammography device according to the related art, pressing pressure of the pressing pad is generally adjusted by manual value, but a pressing velocity thereof is generally constant. That is, in the mammography device according to the related art, the pressing pad is controlled by a uniform manual value regardless of the biological index of the subject, such that a photographing environment appropriate for the subject is not provided. Therefore, the subject feels large pain and discomfort. Further, when the subject moves due to the pain and the discomfort, an accurate x-ray image may not be obtained.

DISCLOSURE

Technical Problem

Therefore, the present invention has been made to solve the above-mentioned problems of the related art. An object of the present invention is to provide a mammography device capable of a mammography device capable of providing comfort to a subject and accomplishing a high photographing accuracy by removing or minimizing pain or discomfort applied to the subject, and a method of photographing an object to be inspected using the same.

Technical Solution

According to an aspect of the present invention, there is provided a mammography device including: a generator irradiating an X-ray; a detector facing the generator; a pressing pad moving between the generator and the detector to press an object to be inspected; a biological index deciding unit deciding a biological index of a subject; and a controller controlling a movement distance and a velocity of the pressing pad on the basis of the biological index decided in the biological index deciding unit.

The biological index may include one or more selected from the group consisting of an age, a sex, a height, a weight, pregnancy, a size of a breast, a density of the breast, and a body mass of the subject.

The biological index deciding unit may include a biological index sensing unit including one or more selected from the group consisting of a breast size measurer, a breast density measurer, and a body mass measurer.

The controller may move the pressing pad depending on a condition selected from the group consisting of a uniform velocity, an acceleration, a deceleration, and a combination thereof.

According to another aspect of the present invention, there is provided a method of photographing an object to be inspected, including: providing a mammography device including a generator irradiating an X-ray, a detector facing the generator, and a pressing pad moving between the generator and the detector to press the object to be inspected; deciding a biological index of a subject; and pressing the object to be inspected while controlling a movement distance and a velocity of the pressing pad on the basis of the decided biological index of the subject.

The pressing of the object to be inspected may include: determining the movement distance and the velocity of the pressing pad on the basis of the decided biological index of the subject; and moving the pressing pad at the determined moving distance and velocity of the pressing pad.

The deciding of the biological index of the subject may include receiving data obtained from a biological index sensing unit including one or more selected from the group consisting of a breast size measurer, a breast density measurer, and a body mass measurer.

In the pressing of the object to be inspected, the pressing pad may move depending on a condition selected from the group consisting of a uniform velocity, an acceleration, a deceleration, and a combination thereof.

Advantageous Effects

As described above, in the mammography device and the method of photographing an object to be inspected using the same according to an exemplary embodiment of the present invention, pain or discomfort applied to the subject may be removed or minimized to provide comfort to the subject. Further, since X-ray photographing may be performed in this comfortable state, a high photographing accuracy may be accomplished, such that the number of times of unnecessary photographing is decreased, thereby making it possible to decrease exposure to X-ray.

DESCRIPTION OF DRAWINGS

FIG. 1 is a perspective view illustrating an entire configuration of a mammography device according to an exemplary embodiment of the present invention.

FIG. 2 is a perspective view illustrating some components including a controller and a driving part of a pressing pad configuring the mammography device according to an exemplary embodiment of the present invention.

FIG. 3 is a block diagram of a controller configuring the mammography device according to an exemplary embodiment of the present invention.

FIG. 4 is a flow chart illustrating a method of photographing an object to be inspected using the mammography device according to an exemplary embodiment of the present invention.

FIGS. 5 to 9 are graphs illustrating a correlation between a time and a movement distance of a pressing pad in the method of photographing an object to be inspected using the mammography device according to an exemplary embodiment of the present invention.

BEST MODE

Additional objects, features, and advantages of the present invention may be more clearly understood from the following detailed description and the accompanying drawings. Prior to a detailed description of the present invention, the present invention may be variously modified and altered and have several exemplary embodiments. Examples described below and illustrated in the drawings are not to limit the present invention to specific exemplary embodiments. In addition, various modifications, alterations, and amendments may be made in the scope of the following claims, and it may be understood that these modifications, alterations, and amendments fall within the scope of the present invention.

It is to be understood that when one element is referred to as being "connected to" or "coupled to" another element, it may be connected directly to or coupled directly to another element or be connected indirectly to or coupled indirectly to another element with the other element intervening therebetween. On the other hand, it is to be understood that when one element is referred to as being "connected directly to" or "coupled directly to" another element, it may be connected to or coupled to another element without the other element intervening therebetween.

Terms used in the present specification are used only in order to describe specific exemplary embodiments rather than limiting the present invention. Singular forms include plural forms unless the context clearly indicates otherwise. It will be further understood that terms "include", "have", or the like, used in the present specification are to specify the presence of features, numerals, steps, operations, components, parts mentioned in the present specification, or a combination thereof, but do not preclude the presence or addition of one or more other features, numerals, steps, operations, components, parts, or a combination thereof.

A term "part", "-er/or", "unit", "module", or the like, described in the present specification means a processing unit of at least one function or operation and may be implemented by hardware or software or a combination of hardware and software.

In describing the present invention with reference to the accompanying drawings, the same components will be denoted by the same reference numerals, and an overlapped description therefor will be omitted. When it is decided that a detailed description for the known art related to the present invention may unnecessarily obscure the gist of the present invention, the detailed description will be omitted.

Hereinafter, a digital mammography device according to an exemplary embodiment of the present invention will be described in detail with reference to the accompanying drawings. Although a digital type mammography device has been described as an example of a "mammography device" in the present specification, the present invention is not limited thereto, but may also be applied to an analog type mammography device.

FIG. 1 is a perspective view illustrating an entire configuration of a mammography device according to an exemplary embodiment of the present invention, and FIG. 2 is a perspective view illustrating some components including a controller and a driving part of a pressing pad configuring the mammography device according to an exemplary embodiment of the present invention.

As illustrated in FIG. 1, the mammography device according to an exemplary embodiment of the present invention is configured to include a device body 100 including basic components for X-ray photographing and a support column 200 to which the device body 100 is connected to be vertically movable. The support column 200, which is a support having a lower end portion fixed to a bottom and having a vertical column shape, provides a vertical axis to the device body 100 so that the device body 100 may ascend or descend in a vertical length direction.

The device body 100 has an arc shape in which upper and lower (both) end portions thereof face each other, and is called a C arm since it generally has a C shape or a shape similar to the C shape. The device body 100 includes a column connection part 110 connected to the support column 200 so as to ascend or descend in the vertical direction and a vertical connection part 120 connected to the column connection part 110 so as to be rotatable with respect to the column connection part 110. The device body 100 includes a generator 130 mounted at one end portion (for example, an upper end portion in the present exemplary embodiment) of the vertical connection part 120 of the device body 100 and irradiating an X-ray toward the other end portion (for example, a lower end portion in the present exemplary embodiment) of the vertical connection part 120 facing one end portion of the vertical connection part 120, a detector 140 mounted at the other end portion of the vertical connection part 120 and facing the generator 130, and a pressing pad 150 linearly reciprocating between the generator 130 and the detector 140 along an inner surface of the device body 100. An object to be inspected is positioned between the pressing pad 150 and the detector 140, and X-ray photographing is performed on the object to be inspected. Alternatively, an inspection plate 160 may be selectively installed between the pressing pad 150 and the detector 140, the object to be inspected may be positioned between the pressing pad 150 and the inspection plate 160, and X-ray photographing may be performed on the object to be inspected.

The vertical connection part 120 is connected to the column connection part 110 so as to be rotatable with respect to a horizontal axis so that a breast may be photographed by a mediolateral oblique view, and a rotation driving part (not illustrated) for rotating the vertical connection part 120 as described above is installed at the column connection part 110.

The vertical connection part 120 basically includes upper and lower (both) end portions at which the generator 130 and the detector 140 are mounted, respectively, and two columns 121 connecting the upper and lower (both) end portions to each other, as illustrated in FIG. 2. The vertical connection part 120 includes a driving motor 122, which is a driving means for vertically moving the pressing pad 150, disposed at an upper end portion thereof, a pulley 126 installed at a lower end portion thereof, and a driving belt 124 being across a shaft of the driving motor 122 and the pulley 126 disposed at the lower end portion of the vertical connection part 120. A pressing pad support part 152 is slidably connected to the two Columns 121 of the vertical connection part 120, and one side of the driving belt 124 is fixed and connected to the pressing pad support part 152. Through the above-mentioned configuration, as the driving motor 122 rotates, the driving belt 124 vertically moves, such that the pressing pad support part 152 vertically moves. Here, the pressing pad 150 is fixed to a front end portion of the pressing pad support part 152, such that the pressing pad 150 vertically moves together with the pressing pad support part 152. The breast positioned on the detector 140 or on the inspection plate 160 in some cases is pressed by the above-mentioned vertical movement of the pressing pad 150.

The generator 130 mounted at an upper end portion of the device body 100 is a device allowing electrons having high kinetic energy to collide with a metal target to generate an X-ray, and preferably includes an optical system such as a collimator, or the like, controlling an irradiation direction or an irradiation area of the X-ray.

The detector 140 mounted at a lower end portion of the device body 100 basically is a means for receiving the X-ray passing through the breast to obtain an image, and since the breast is put on the detector 140, the detector 140 may also serve as a support part for the object to be inspected for supporting the breast. That is, the breast is put on the detector 140 and is then pressed by the pressing pad 150, such that the breast is pressed between the detector 140 and the pressing pad 150, and the breast in a state in which it is pressed as described above is photographed by the generator 130 and the detector 140. The detector 140 generates an electric signal for each position that is in proportion to an amount of incident X-ray, and reads the electrical signal and position information and processes the read electrical signal and position information by an image processing algorithm, thereby making it possible to obtain an X-ray image of the breast. Here, a general technology content such as a direct converting scheme of obtaining the electrical signal directly from the X-ray without having a separate intermediate step, an indirect converting scheme of obtaining the electrical signal indirectly by a visible ray converted from the X-ray, or the like, depending on a scheme of converting the X-ray may be widely applied to the detector 140.

The inspection plate 160 may be included as a selective component in order to substitute for a function of the detector 140 as the support part for the object to be inspected. In the case in which the inspection plate 160 is included, the breast is pressed by the pressing pad 150 and the inspection plate 160, and the breast in this state is photographed by the generator 130 and the detector 140. Therefore, the detector 140 performs only a function of receiving the X-ray passing through the breast to obtain the image.

In the mammography device configured as described above, the driving motor 122 is driven by a controller 300 in order to press the breast positioned on the detector 140 or on the inspection plate 160 in some cases. The controller 300 is a component for controlling all of the components of the mammography device, and functions of the controller 300 other than a function of controlling movement of the pressing pad 150 are the same as those of a controller of a mammography device according to the related art. That is, the function of controlling movement of the pressing pad 150 may be functionally added to a controller of a mammography device that has been installed in advance. Unlike this, the controller 300 is provided in a sub-controller form to control only the movement of the pressing pad 150, and other components of the mammography device may also be controlled by a separate main controller. In the present specification, in any case, only the function of the controller 300 of controlling movement of the pressing pad 150 will be described.

As illustrated in FIG. 2, the controller 300 receives a biological index from a biological index input unit 410 and/or a biological index sensing unit 420 and drives the driving motor 122 on the basis of the biological index to vertically move the pressing pad support part 152 and the pressing pad 150 connected to the pressing pad support part 152 at a desired distance and velocity, thereby pressing the breast positioned on the detector 140 or on the inspection plate 160 in some cases. For convenience, the biological index input unit 410 and/or the biological index sensing unit 420 will be called a biological index deciding unit.

The controller 300, which is a main component of the present invention, will be described in detail with reference to FIGS. 2 and 3. FIG. 3 is a block diagram of a controller 300 configuring the mammography device according to an exemplary embodiment of the present invention.

As illustrated in FIGS. 2 and 3, the biological index deciding unit of the mammography device according to an exemplary embodiment of the present invention includes the biological index input unit 410 input biological indices of different subjects and/or the biological index sensing unit 420 sensing the biological indices of the subjects.

The biological index input unit 410, which is a unit through which a manager is to input the biological index of the subject figured out at the outside of the mammography device, for example, an age, a sex, a height, a weight, pregnancy, and the like, may include a keyboard connected to the mammography device, a touch panel of a monitor, a remote controller, and the like.

The biological index sensing unit 420, which is a unit measuring a biological index of the subject within the mammography device, includes a measurer measuring a size and/or a density of a breast of the subject, and a measurer measuring a body mass of the subject, and the like. The biological index sensing unit 420 may be installed at one side of the mammography device, preferably, one side of the device body 100.

Next, a configuration and an operation of the controller 300 controlling the movement of the pressing pad 150 by a value input by the biological index input unit 410 and/or sensed and measured by the biological index sensing unit 420 will be described with reference to FIG. 3.

The controller 300 includes a pressing velocity adjusting unit 320 including a biological index data receiving unit 322, a pressing velocity determining unit 324, and a motor controlling unit 326, and a pressing velocity database DB 340.

The biological index data receiving unit 322 of the pressing velocity adjusting unit 320 receives biological index data from the biological index input unit 410 and/or the biological index sensing unit 420 and transfers the biological index data to the pressing velocity determining unit 324. The pressing velocity determining unit 324 communicates with the pressing velocity database DB 340 to match a pre-stored movement distance and a velocity of the pressing pad 150 to the pressing velocity database DB 340 depending on the biological index data, thereby determining a final movement distance and a velocity of the pressing pad 150. The pressing velocity determining unit 324 transfers data on the determined final movement distance and the determined velocity of the pressing pad 150 to the motor controlling unit 326, and the motor controlling unit 326 controls an operation of the driving motor 122 depending on the received data. Here, the pressing velocity database DB 340 may store a movement distance and a velocity of the pressing pad 150 for each biological index in a table form, and be mounted in a memory mounted inside/outside the controller 300 or a console personal computer connected to the mammography device.

Next, a method of X-ray photographing a breast of a subject using the mamma mammography device according to an exemplary embodiment the present invention will be described to FIG. 4. FIG. 4 is a flow chart illustrating a method of photographing an object to be inspected using the mammography device according to an exemplary embodiment of the present invention. As illustrated in FIG. 4, the method of photographing an object to be inspected using the mammography device according to an exemplary embodiment of the present invention is as follows.

The method of photographing an object to be inspected using the mammography device according to an exemplary embodiment of the present invention includes accurately positioning a subject photographing position of the mammography device in a standing or sitting state (st1) and inputting and/or measuring a biological index of the subject through the biological index input unit 410 and/or the biological index sensing unit 420 (st2). A sequence of these steps st1 and st2 may also be changed. For step st1, the device body 100 adjusts a position of the detector 140 (or the inspection plate 160 in some cases) so as to be appropriate for a position of the breast of the subject while vertically moving along the support column 200. The adjustment of the position is automatically or manually performed, and it is preferable that a step of measuring or inputting the position of the breast of the subject is first performed in order to automatically perform the adjustment of the position. In this case, data on the position of the breast of the subject are additionally input and/or measured through the biological index input unit 410 and/or the biological index sensing unit 420 in step st2 while changing a sequence of steps st1 and st2, thereby making it possible to automatically adjust the position of the detector 140.

Then, when the biological index of the subject is input and/or measured, a step st3 of determining a movement distance and a velocity of the pressing pad 150 in the controller 300 is performed. In this case, as described above, the biological index data receiving unit 322 of the controller 300 receives the biological index of the subject input and/or measured through the biological index input unit 410 and/or the biological index sensing unit 420 in step st2, and the pressing velocity determining unit 324 of the controller 300 determines the movement distance and the velocity of the pressing pad 150 on the basis of the received biological index data while communicating with the pressing velocity database DB 340.

When the movement distance and the velocity of the pressing pad 150 are determined in step st3, the motor controlling unit 326 of the controller 300 drives the driving motor 122 to move the pressing pad 150 at the determined movement distance and the determined velocity, thereby performing the pressing of the breast (step st4). When the corresponding pressing is completed, a step (st5) of X-ray photographing the object to be inspected is performed, such that the method of photographing an object to be inspected ends.

In the method of photographing an object to be inspected as described above, a correlation between a time and a movement distance of a pressing pad will be described with reference to FIGS. 5 to 9. FIGS. 5 to 9 are graphs illustrating a correlation between a time and a movement distance of a pressing pad 150 in the method of photographing an object to be inspected using the mammography device according to an exemplary embodiment of the present invention. In these graphs, a case in which distances at which the pressing pad 150 finally arrives are the same as each other by changing a movement distance of the pressing pad 150 depending on a time, that is, a pressing velocity when sizes of breasts are the same as each other are described by way of example.

A change in a movement distance of the pressing pad 150 depending on a time may be mainly divided into two groups (four cases). A first group (FIGS. 5 and 6) is cases in which a movement distance of the pressing pad 150 is linear (case 1 (C11 and C12)) or non-linear (case 2 (C21 and C22)) from an initial position Do until completion Df of the pressing. A second group (FIGS. 7 and 8) is cases in which a movement distance of the pressing pad 150 is divided into a first section Do to Dc from an initial position Do until a contact between the pressing pad 150 and the breast and a second section Dc to Df from the contact between the pressing pad 150 and the breast until completion Df of the pressing, and is linear in the first section Do to Dc and is linear (case (C31 and C32)) or non-linear (case 4 (C41 and C42)) in the second section Dc to Df. Meanwhile, dotted lines denoted by C0 graphs of FIGS. 5 to 9, which are cases of a mammography device according to the related art, indicate movement distances, depending on a time, of the pressing pad moving at a fixed constant velocity.

First, graphs illustrated in FIG. 5 are a case in which a movement distance of the pressing pad 150 is linearly increased depending on a time, that is, a case (case 1 (C11 and C12)) in which a velocity of the pressing pad 150 is constant, in the first group. As compared with a case C0 of the pressing pad 150 moving at a fixed constant velocity in the mammography device according to the related art, in the mammography device according to a exemplary embodiment of the present invention, the pressing pad 150 may move at a uniform velocity (C11) higher than or at a uniform velocity (C12) lower than that of the related art. In the case in which the pressing is applied at the high uniform velocity (C11), the pressing of the breast is completed in a rapid time tf11. On the other hand, in the case in which the pressing is applied at the low uniform velocity (C12), a time tf12 in which the pressing of the breast is completed becomes long. The pressing velocity may be appropriately determined between C11 and C12 depending on the biological index of the subject.

Graphs illustrated in FIG. 6 are a case in which a movement distance of the pressing pad 150 is decreased or increased, that is, a case (case 2 (C21 and C22)) in which the pressing pad 150 moves a deceleration or an acceleration, in the first group. A graph C21 illustrates a case in which a pressing velocity of the pressing pad 150 is gradually decreased from an initial position Do until completion Df of the pressing, and a graph C22 illustrates a case in which a pressing velocity of the pressing pad 150 is increased from an initial position Do until completion Df of the pressing. These cases are a case (C21) in which the breast is rapidly pressed at an initial point in time and is then slowly pressed at a point in time at which the pressing is completed and a case (C22) in which the breast is slowly pressed at an initial point in time and is then rapidly pressed at a point in time at which the pressing is completed, and a change level of the pressing velocity may be appropriately determined depending on a biological index.

Next, graphs illustrated in FIG. 7 are a case (case 3 (C31 and C32)) in which the pressing pad 150 moves at a velocity increased or decreased to a predetermined value from after a point in time tc at which the pressing pad 150 moves at a constant velocity to contact the breast until completion Df of the pressing, in the second group. A graph C31 illustrates a case in which a pressing velocity of the pressing pad 150 is increased to a predetermined value after the pressing pad contacts the breast. In the graph C31, when a velocity of the pressing pad 150 is divided into a first velocity V1 of a section Do to Dc from an initial position Do to a contact position Dc and a second velocity V2 of a section Dc to Df from the contact position Dc to a pressing completion position Df, V1<V2 is satisfied. In addition, a graph C32 illustrates a case in which a pressing velocity of the pressing pad 150 is decreased to a predetermined value after the pressing pad contacts the breast. In the graph C32, when a velocity of the pressing pad 150 is divided into a first velocity V1 of a section Do to Dc from an initial position Do to a contact position Dc and a second velocity V2 of a section Dc to Df from the contact position Dc to a pressing completion position Df, V1>V2 is satisfied.

Graphs illustrated in FIG. 8 are a case (case 4 (C41 and C42)) in which the pressing pad 150 moves at a gradually increased velocity or a gradually decreased velocity, that is, at an acceleration or a deceleration, from after a point in time tc at which the pressing pad 150 moves at a constant velocity to contact the breast until completion of the pressing, in the second group. A graph C41 illustrates a case in which a pressing velocity Of the pressing pad 150 is gradually increased after the pressing pad contacts the breast. In the graph C41, when a velocity of the pressing pad 150 is divided into a first velocity V1 of a section Do to Dc from an initial position Do to a contact position Dc and a second velocity V2 of a section Dc to Df from the contact position Dc to a pressing completion position Df, V1 is constant and V2 is increased. A graph C42 illustrates a case in which a pressing velocity of the pressing pad 150 is gradually decreased after the pressing pad contacts the breast. In the graph C42, when a velocity of the pressing pad 150 is divided into a first velocity V1 of a section Do to Dc from an initial position Do to a contact position Dc and a second velocity V2 of a section Dc to Df from the contact position Dc to a pressing completion position Df, V1 is constant and V2 is decreased.

In addition to these four cases, as illustrated in FIG. 9, an increase and a decrease in the pressing velocity (C5) may also be repeated after a point in time tc at which the pressing pad 150 moves at a constant velocity to contact the breast. In this case, when pressing the breast while repeatedly alleviating the pressing applied to the breast, the entire pain may be decreased. This may be a form in which C41 and C42 in FIG. 8 are combined with each other. As described above, the movement of the pressing pad 150 may be implemented by combinations in several forms in addition to forms illustrated in FIGS. 5 to 9.

As described above, in the mammography device and the method of photographing an object be inspected using the same according to an exemplary embodiment of the present invention, a high photographing accuracy may be provided, and pain or discomfort applied to the subject may be removed or minimized to provide comfort to the subject.

It will be obvious to those skilled in the art to which the present invention pertains that the present invention described above is not limited to the above-mentioned exemplary embodiments and the accompanying drawings, but may be variously substituted, modified, and altered without departing from the scope and spirit of the present invention.

The invention claimed is:

1. A mammography device comprising:
   a generator irradiating an X-ray;
   a detector facing the generator;
   a pressing pad moving between the generator and the detector to press an object to be inspected; a biological index deciding unit deciding a biological index of a subject; and
   a controller controlling a movement distance and a velocity of the pressing pad on the basis of the biological index decided in the biological index deciding unit.

2. The mammography device according to claim 1, wherein the biological index includes one or more selected from the group consisting of an age, a sex, a height, a weight, pregnancy, a size of a breast, a density of the breast, and a body mass of the subject.

3. The mammography device according to claim 1, wherein the biological index deciding unit includes a biological index sensing unit including one or more selected from the group consisting of a breast size measurer, a breast density measurer, and a body mass measurer.

4. The mammography device according to claim 1, wherein the controller moves the pressing pad depending on a condition selected from the group consisting of a uniform velocity, an acceleration, a deceleration, and a combination thereof.

5. A method of photographing an object to be inspected, comprising:
   providing a mammography device including a generator irradiating an X-ray, a detector facing the generator, and
   a pressing pad moving between the generator and the detector to press the object to be inspected;
   deciding a biological index of a subject; and pressing the object to be inspected while controlling
   a movement distance and a velocity of the pressing pad on the basis of the decided biological index of the subject.

6. The method of photographing an object to be inspected according to claim 5, wherein the pressing Of the object to be inspected includes:
   determining the movement distance and the velocity of the pressing pad on the basis of the decided biological index of the subject; and
   moving the pressing pad at the determined moving distance and velocity of the pressing pad.

7. The method of photographing an object to be inspected according to claim 5, wherein the biological index includes one or more selected from the group consisting of an age, a sex, a height, a weight, pregnancy, a size of a breast, a density of the breast, and a body mass of the subject.

8. The method of photographing an object to be inspected according to claim 5, wherein the deciding of the biological index of the subject includes receiving data obtained from a biological index sensing unit including one or more selected from the group consisting of a breast size measurer, breast density measurer, and a body mass measurer.

9. The method of photographing an object to be inspected according to any one of claims 5 to 8, wherein in the pressing of the object to be inspected, the pressing pad moves depending on a condition selected from the group consisting of a uniform velocity, an acceleration, a deceleration, and a combination thereof.

* * * * *